United States Patent [19]

Turner

[11] Patent Number: 4,564,035
[45] Date of Patent: Jan. 14, 1986

[54] TOOTHPICK HOLDER

[76] Inventor: Tomie L. Turner, 3220 Anderson Dr., Lithia Springs, Ga. 30057

[21] Appl. No.: 652,672

[22] Filed: Sep. 21, 1984

[51] Int. Cl.$^4$ ............................................. A61C 15/00
[52] U.S. Cl. ...................................................... 132/90
[58] Field of Search .................................... 132/90, 91

[56] References Cited

U.S. PATENT DOCUMENTS

| | | | |
|---|---|---|---|
| 451,293 | 4/1891 | Naylor | 81/28 |
| 592,838 | 11/1897 | Solem | 15/146 |
| 736,101 | 8/1903 | Hough | 279/9 R |
| 792,471 | 6/1905 | Smith | 132/93 |
| 797,684 | 8/1905 | Harper | 433/147 |
| 1,291,282 | 1/1919 | Usher | 132/89 |
| 1,296,067 | 3/1919 | Fuller | 15/176 |
| 2,573,201 | 10/1951 | Kelley et al. | 15/132.5 |
| 3,204,275 | 9/1965 | Baker | 15/172 |
| 3,559,226 | 2/1971 | Burns | 15/167 |
| 3,660,902 | 5/1972 | Axelsson | 32/58 |
| 3,892,040 | 7/1975 | Marquis | 32/40 |
| 4,033,007 | 7/1977 | Hadary | 132/90 |
| 4,397,327 | 8/1983 | Hadary | 132/90 |

FOREIGN PATENT DOCUMENTS

| | | | |
|---|---|---|---|
| Ad.8803 | of 1908 | United Kingdom | 132/190 |
| 191896 | 1/1923 | United Kingdom | 132/90 |

*Primary Examiner*—Gregory E. McNeill
*Attorney, Agent, or Firm*—Thomas & Kennedy

[57] ABSTRACT

A toothpick holder has a rod-shaped member (20) slidably located within a tubular member (30) and a nut (38) threaded on a threaded end (21) of the member (20). Rotation of the nut (38) brings an enlarged head (22) of member (20) towards a slotted end of the tubular member in a manner to apply a gripping force on a toothpick positioned in a channel (27) and troughs (28) formed in the head (22) without the application of shearing forces to the toothpick.

9 Claims, 7 Drawing Figures

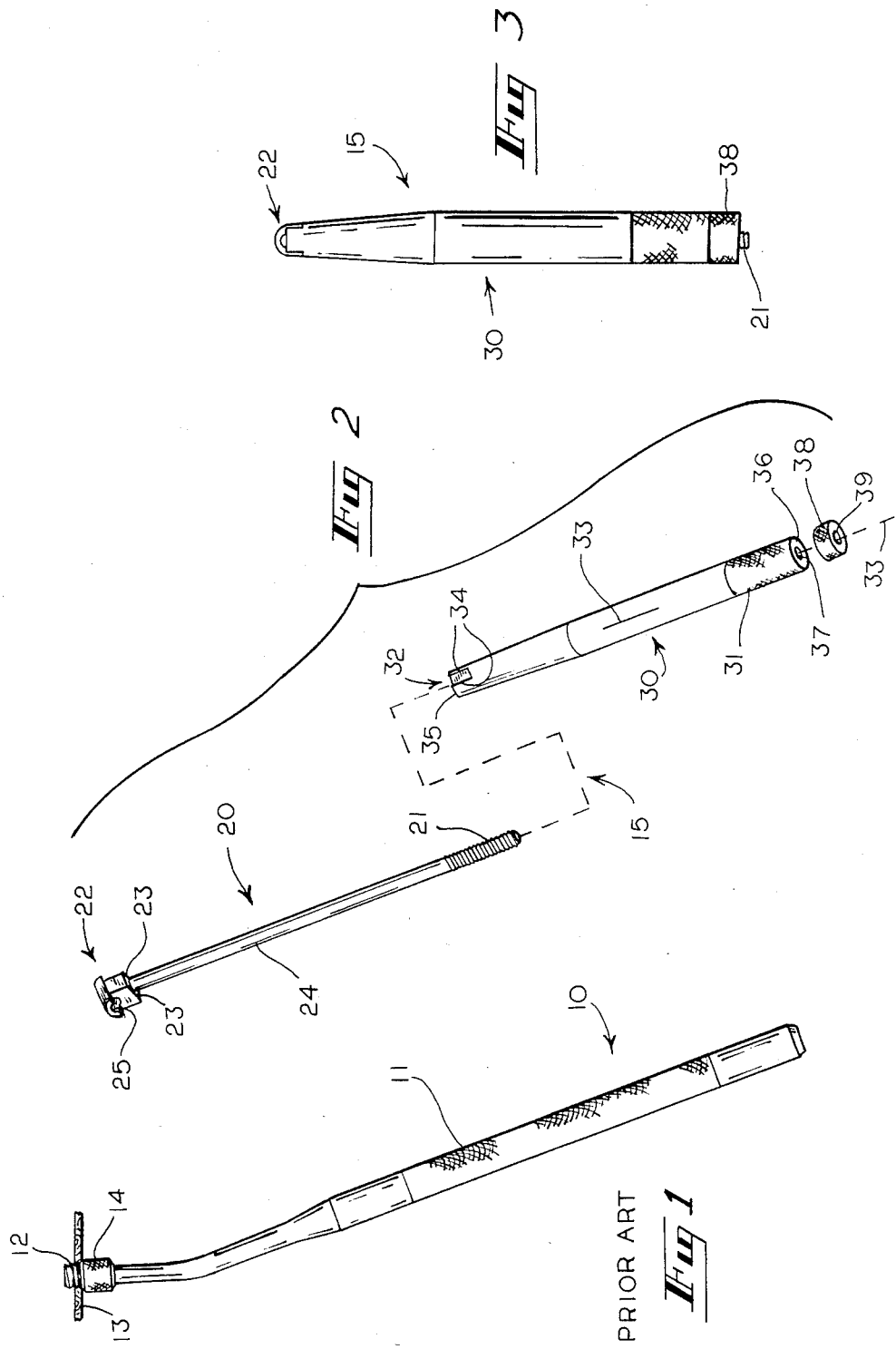

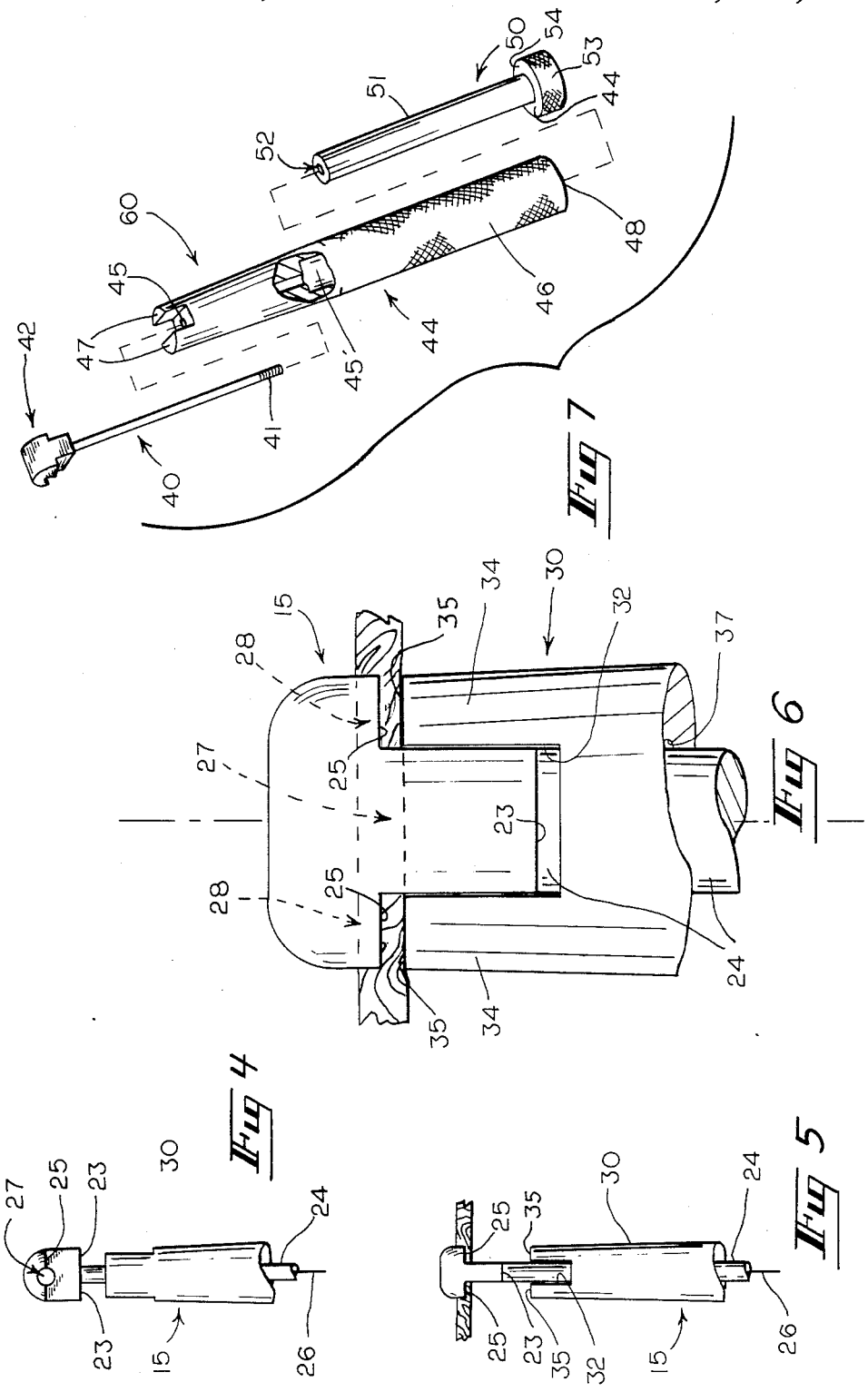

TOOTHPICK HOLDER

This invention relates generally to dental instruments, and particularly to toothpick holders.

BACKGROUND OF THE INVENTION

Toothpicks are widely used in cleaning the interproximal spaces between human teeth and in massaging and strengthening gums that surround the teeth. Typically, the picks, which are formed of wood or plastic, are about two inches in length. This length, however, makes then awkward to manipulate within the mouth. To solve this problem by merely making them smaller would, however, create additional problems such as the risk of loosing manual hold during use.

Heretofore, toothpick holders have been devised to overcome the just described problem and to facilitate oral manipulation. As exemplified by the toothpick holder disclosed in U.S. Pat. No. 3,892,040, toothpick holders typically have been in the form of an elongated handle having a channel formed in one end in which a toothpick is supported at a right angle to the handle.

Unfortunately, some of the prior art toothpick holders have problems associated with their use. For example in one type toothpick holder a nut surrounds the handle and when a toothpick is inserted through the toothpick support hole in the handle the nut is screwed about the handle until it partially covers the hole and engages and holds the toothpick. This applies a shearing force by the nut to the toothpick. This shearing force often results in the toothpick being fractured at the point where it emerges from the hole in the handle. In addition, manual manipulation of the nut in the region of the toothpick brings the manipulator's fingers into contact with the toothpick itself and to that portion of the holder which is inserted into the mouth. This, of course, is not conducive to good oral hygiene. Accordingly, were a toothpick holder to be devised which is inexpensive to produce, easy to use and which overcomes these problems, a distinct advance in the art would be achieved. Thus, it is to the provision of such a toothpick holder that the present invention is primarily directed.

SUMMARY OF THE INVENTION

Briefly described, the present invention comprises a toothpick holder including a rod-shaped member having a flange formed on one end thereof that provides a ledge which extends substantially at a right angle with respect to the longidinal axis of the member. This one end is also formed with a channel that extends transversely to the longitduianl axis of the rod member and which merges with a trough that is formed in the ledge. The toothpick holder also comprises a tubular handle member adapted to be telescopically positioned over the rod-shaped member with an end of the tubular handle member moved into engagement with the ledge of the rod-shaped member. So constructed, a toothpick placed in the channel and into the trough is gripped by the holder without applying shearing forces to the toothpick.

The tubular handle member is slidably positioned about the rod-shaped member with one end of the handle member located adjacent the channel of the rod member and the other end of the handle member located adjacent the threads of the rod member. A nut is threaded onto the threads of the rod member adjacent the base of the tubular handle member. With this construction the toothpick holder tubular member can be used into gripping engagement with a toothpick extending out of the channel of the rod member by screwing the nut against the base of the tubular member.

BRIEF DESCRIPTION OF THE DRAWINGS

FIG. 1 is a side elevational view of a toothpick holder of the prior art.

FIG. 2 is a perspective view of a toothpick holder embodying principles of the present invention shown in a disassembled configuration.

FIG. 3 is a side elevational view of the toothpick holder illustrated in FIG. 2 shown in an assembled configuration.

FIG. 4 is an enlarged, side elevational view of an end portion of the toothpick holder illustrated in FIG. 3 with two holder members shown slightly separated for purposes of illustration.

FIG. 5 is a side elevational view of the holder shown in in FIG. 4 with the holder rotated 90° and with the holder shown loosely supporting a toothpick.

FIG. 6 is a further enlarged, side elevational view of the end portion of the holder shown in FIG. 5 with the two holder members drawn together into gripping engagement with the toothpick.

FIG. 7 is a perspective view of a toothpick holder embodying principles of the invention in an alternative form shown in a disassembled configuration.

DETAILED DESCRIPTION

Referring now in more detail to the drawings, in which like numerals indicate like parts throughout the several views, FIG. 1 shows a toothpick holder 10 of the prior art having an elongated, rod-shaped member 11 formed with screw threads 12 at one end thereof. The holder is shown gripping a toothpick 13 which extends through an unshown channel formed through the threaded end. The toothpick is held snuggly to the holder by a threaded nut 14 which has been screwed upon the threads 12 into gripping engagement with the toothpick after the toothpick had been positioned within the channel. As previously explained, problems with toothpick holders of this type include the fact that manual manipulation of the holder is performed at the holder end which grips the toothpick. This necessitates a procedure that usually brings human fingers into contact with that portion of the holder which is inserted into the mouth and often brings the fingers into contact with the toothpick itself, resulting in poor hygienic practices. It is also seen that as the nut 14 is threaded upon threads 12 into engagement with the toothpick 13 that the nut applies a shearing force to the toothpick which can easily cause it to fracture. Indeed, continued forced rotation of the nut after it has made contact with the toothpick can effect a complete severance of the toothpick.

With reference next to FIGS. 2–6, a toothpick holder 15 embodying principles of the present invention which overcomes these problems is seen to include an elongated, rod-shaped member 20 having screw threads 21 formed on one end thereof and an enlarged, "mushroom" head, indicated generally at 22, formed on the other end thereof. The head 22 generally is in the shape of a two-step flange. The first step presents two coplanar, flat ledges 23 which project to either side of a cylindrical stem portion 24 of the rod member and extends perpendicular to the longitudinal axis 26 of the rod member. The other step provides two coplanar, flat ledges 25 which also extend normally to to the axis 26 of the cylindrical rod 24 but at 90° from the direction of the extension of the ledge 23. A cylindrical channel 27 extends completely through the enlarged head transversely to the rod-shaped member axis 26. Approximately half of the channel is located above the ledges 25 while the other half of the channel is located below them. The ends of the cylindrical channel 27 merge with semicylidrical troughs 28 that are formed in the ledges 25.

With continued reference to FIGS. 2-6, the toothpick holder is further seen to include an elongated, tubular member or handle 30 having knurls formed on one external end portion 31 (FIG. 2) and a slot 32 extending transversely to the longitudinal axis 33 of the tubular member formed in the opposite end. The slot 32 is straddled by two walls 34 that terminate in two coplanar, flat ends 35. The other, knurled end 31 also has a flat wall or base 36 extending normally to the axis 33 about an outlet of an unthreaded longitudinal channel 37 that extends completely through the tubular member along axis 33. The channel 37 is sized to permit the rod 24 including threads 21 to slide easily threthrough but without appreciable, lateral play. The holder also includes a knurled nut 38 having threads formed along its bore 39 adapted to be screwed upon the threads 21 of the rod-shaped member 20. The end of the nut shown positioned adjacent the end 36 of the tubular handle member 30 also is flat so that it makes flush engagement with that end.

In use, the rod-shaped member 20 is telescopically slid into the tubular member 30 and the nut 38 threaded onto the end of threads 21 with the ledges 23 of head 22 located within the slot 32. In this relative position of the holder members 20 and 30, which axially locates the head 22 relative to the slotted end of the tubular member between the positions shown in FIG. 3 and FIG. 4, that portion of the head slidably located within slot 32 functions as a key in preventing relative, rotary movement between the rod-shaped and the tubular members. When the holder 15 is loosely assembled as described, a toothpick is positioned within the channel 27 and troughs 28. Nut 38 is next screwed on threads 21 thereby bringing it into flush contact with the end 36 of the tubular member. Continued screwing of the nut then draws the head 22 of the rod member 20 further down into the slotted end of the tubular member. As this is done the flat ends 35 and the semicylindrical troughs 28 are brought firmly against opposite sides of the toothpick in a vice-like, squeezing action but without the application of appreciable shearing forces. The resistance this effects causes the nut 38 also to be held snuggly to the end of the tubular member. The toothpick itself is now firmly held to the holder for oral use.

With reference next to FIG. 7, a toothpick holder 60 embodying principles of the invention in an alternative form is seen to include a rod-shaped member 40 having threads 41 formed on one end thereof and an enlarged, "mushroom" head 42 formed on the other end thereof which is of the same shape as the head 22 which was previously described in detail in conjunction with the description of the embodiment shown in FIGS. 2-6. Thus, the rod-shaped member 40 here is substantially the same as the rod-shaped member 20 in that other embodiment except for the fact that the rod itself is relatively shorter. The toothpick holder here also again includes a tubular handle member 44 having a longitudinal channel 45 extending along its axis completely therethrough. The channel 45 is relatively narrow at the slotted end but merges with an enlarged portion 45 intermediate its ends as shown in the cross-sectioned segment. One end 46 of the tubular member is knurled while the other end is seen to have a transverse slot which divides two coplanar, flat ends 47. The toothpick holder includes another tubular member 50 which has a hollow, cylindrical stem 51 of a size adapted to be accomodated within the enlarged channel portion 45'. The member 51 is, in effect, a nut of specialized configuration having a threaded bore 52 in which the threads 41 of the rod-shaped member 40 may be screwed. The member 50 has a knurled flange 53 formed on one end thereof adapted to have an annular ledge 54 brought into snug engagement with the planar end wall 48 of the knurled end 46 of the tubular member 44.

For use, the members 40 and 50 are inserted into opposite ends of the tubular member 44 and threads 41 screwed into the threaded bore 52 of the larger member 50. With head 42 slidably keyed in the slotted end of, the tubular member 44, a toothpick is placed in the head channel and troughs and the knurled flange 53 movably rotated to bring the holder elements into gripping engagement with the toothpick as described in the discussion of the other embodiment.

When a toothpick has been grasped by the holder 15 or 60, one protruding end of the toothpick can be broken away from the holder, leaving only the other end protruding from the holder. This causes the portion of the toothpick remaining in the holder to form a right angle with respect to the holder, which is ideal for the user in reaching between his teeth with the toothpick. In the meantime, the holder firmly grasps the toothpick with compression forces along a portion of the length of the toothpick, which tends to hold the toothpick without tending to break the toothpick.

It thus is seen that a toothpick holder is now provided which overcomes problems associated with those of the prior art. It should, however, be understood that the just described embodiments merely illustrate principles of the invention in preferred forms. Many modifications, additions, and deletions may be made thereto without departure from the spirit and scope of this invention as set forth in the following claims.

I claim:

1. A toothpick holder comprising a rod-shaped member having a flange formed on one end thereof providing a ledge extending normally to the longitudinal axis of the rod-shaped member and with said one end being formed with an opening extending transversely to said longitudinal axis that merges with a trough formed in said ledge, and a tubular member telescopically positioned about said rod-shaped member and an end of said tubular member movable into engagement with the ledge of said rod-shaped member, the end of said tubular member extending normally to the longitudinal axis of said rod shaped member, and when a toothpick is inserted in the openings of the rod-shaped member the tubular member is moved toward abutment with the ledge of the rod-shaped member to grip the portions of the toothpick extending out of said opening and into said trough substantially without applying shearing forces to the toothpick.

2. A toothpick holder in accordance with claim 1 wherein said tubular member end and portion of said rod-shaped member ledge are each substantially flat whereby they may make flush engagement with each other.

3. A toothpick holder in accordance with claim 1 wherein said rod-shaped member flange provides two coplanar ledges located upon opposite sides of said longitudinal axis with each ledge being formed with a trough, and wherein said opening extends transversely through said rod-shaped member one end and merges with each of said troughs.

4. A toothpick holder in accordance with claim 1 further comprising means operatively located adjacent the other end of said rod-shaped member for urging said tubular member end towards said rod-shaped member ledge.

5. A toothpick holder in accordance with claim 4 wherein said means for urging comprises screw threads formed on said rod-shaped member other end and a nut threaded on said screw threads.

6. A toothpick holder in accordance with claim 5 wherein one portion of said nut is located within said tubular member and another portion is located outside of said tubular member.

7. A toothpick holder in accordance with claim 5 comprising means for inhibiting rotary movement of said rod-shaped member with respect to said tubular member.

8. A toothpick holder in accordance with claim 7 wherein said means for inhibiting rotary movement comprises a slot formed in said tubular member end in which a portion of said rod-shaped member one end is slidably positioned.

9. A toothpick holder comprising an elongated handle having opposed end surfaces and defining an open-ended channel extending longitudinally therethrough and intersecting at least one of said handle end surfaces, a rod member extending through said channel of a size and shape suitable for longitudinal movement through said channel, said rod member defining an opening extending laterally therethrough, said rod member including at one of its ends an enlarged head of a breadth greater than said channel, said enlarged head including laterally extending ledges positioned coextensively with a portion of said opening and facing said handle end surface and oriented approximately parallel to said handle end surface, with said rod member being sized and shaped to move said opening at least partially into said channel as the ledges of said enlarged head approach abutment with said handle end surface, and a fastener for engagement with said handle and said rod member for fastening said rod member in said handle, whereby a toothpick or the like can be inserted into the opening of the rod member, the rod member moved longitudinally through the channel of the handle until the ledges of the enlarged head clamp portions of the toothpick extending beyond the hole into abutment with the handle end surface to hold the toothpick in place substantially without applying shear forces to the toothpick, and the rod member fastened in a static position to the handle by said fastener.

* * * * *